United States Patent
Schilken

(10) Patent No.: US 8,321,474 B2
(45) Date of Patent: Nov. 27, 2012

(54) SYSTEM AND METHOD FOR GENERATING EVALUATION DATA

(75) Inventor: Joerg Schilken, Konz (DE)

(73) Assignee: Agfa HealthCare N.V., Mortsel (BE)

( * ) Notice: Subject to any disclaimer, the term of this patent is extended or adjusted under 35 U.S.C. 154(b) by 300 days.

(21) Appl. No.: 12/338,691

(22) Filed: Dec. 18, 2008

(65) Prior Publication Data

US 2009/0287741 A1    Nov. 19, 2009

(30) Foreign Application Priority Data

Dec. 21, 2007  (EP) .................................... 07124033

(51) Int. Cl.
*G06F 17/00* (2006.01)
*G06F 17/30* (2006.01)

(52) U.S. Cl. ................................ 707/804; 707/999.002

(58) Field of Classification Search .......... 707/802–804, 707/809, 999.001, 999.101, 955, 960, 999.002
See application file for complete search history.

(56) References Cited

U.S. PATENT DOCUMENTS

| | | | |
|---|---|---|---|
| 5,077,666 | A | 12/1991 | Brimm et al. |
| 7,194,451 | B2 * | 3/2007 | Chaudhuri et al. .......... 707/694 |
| 7,401,057 | B2 * | 7/2008 | Eder .............................. 706/20 |
| 2001/0049610 | A1 | 12/2001 | Hazumi |
| 2002/0103811 | A1 | 8/2002 | Fankhauser et al. |
| 2006/0173713 | A1 | 8/2006 | Petro et al. |
| 2008/0021738 | A1 | 1/2008 | Komiya et al. |
| 2008/0065424 | A1 * | 3/2008 | Frick ................................ 705/3 |
| 2008/0235057 | A1 | 9/2008 | Weidenhaupt et al. |

FOREIGN PATENT DOCUMENTS

| | | |
|---|---|---|
| DE | 44 40 178 A1 | 5/1996 |
| DE | 10 2005 005 243 A1 | 8/2006 |
| DE | 10 2006 008 507 A1 | 9/2007 |
| EP | 1 739 605 A1 | 1/2007 |
| WO | 2006/081041 A2 | 8/2006 |
| WO | 2007/052213 A2 | 5/2007 |

OTHER PUBLICATIONS

Chamberlin, Don, "Using the New DB2, IBM's Object-Relational Database System," Morgan Kaufmann Publishers, Inc., San Francisco, CA, pp. 455-465, 1996.
European Search Report dated Jan. 12, 2008, from counterpart European Application No. EP 07124033.7, filed on Dec. 21, 2007.

* cited by examiner

*Primary Examiner* — Marc Filipczyk
(74) *Attorney, Agent, or Firm* — Houston & Associates, LLP

(57) ABSTRACT

The invention relates to a system for generating evaluation data with a data base for storing original data, a memory for storing an evaluation program for the evaluation of original data stored in the data base and a control. In order to achieve rapid and reliable provision of evaluation data, an evaluation order for evaluating original data is generated upon the occurrence of a pre-specified event. It is checked by the control whether an evaluation order has been generated. In the event of an evaluation order being present, the evaluation program stored in the memory is started dependently upon the evaluation order, the evaluation program accessing original data stored in the data base dependently upon the evaluation order and the evaluation data being generated from this.

22 Claims, 12 Drawing Sheets

Fig. 5A

Figure 1:
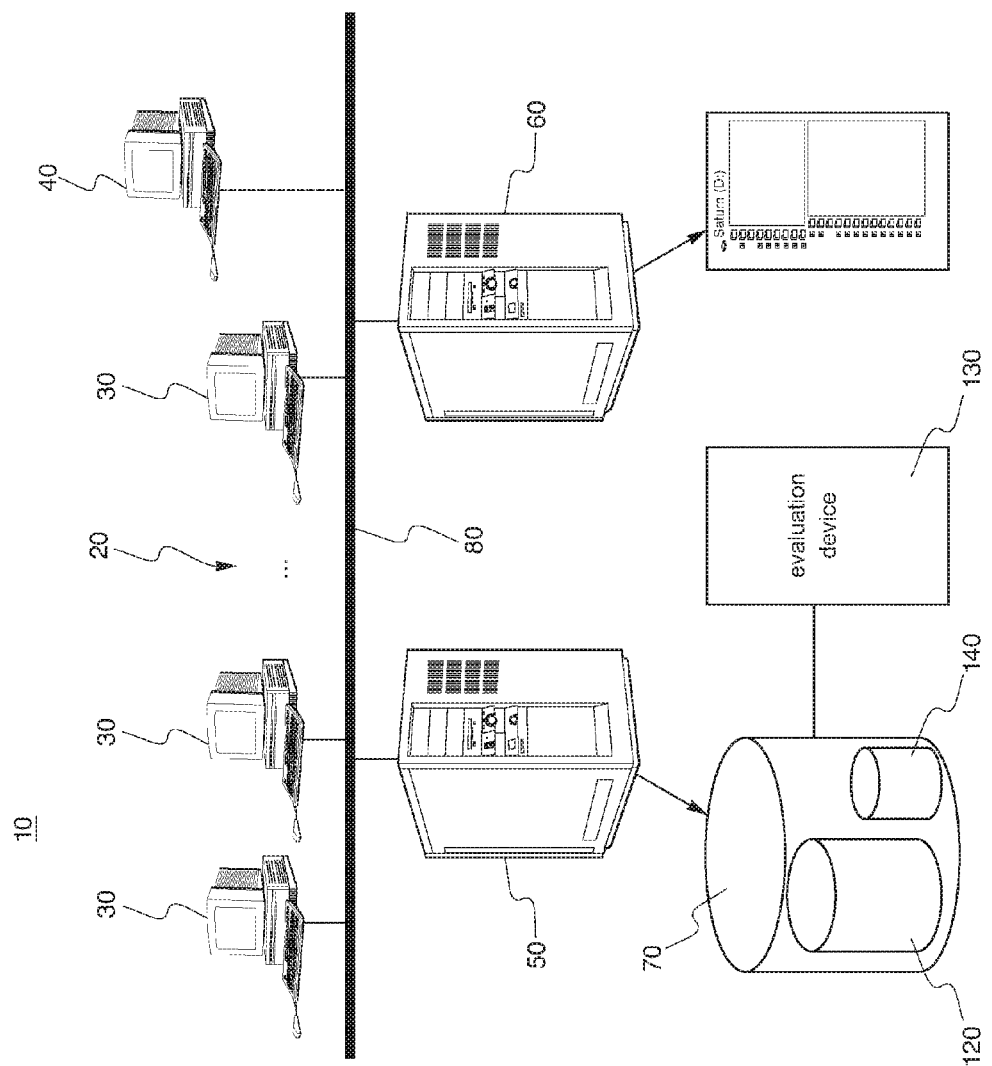

| Midnight Statistics: Department/Station | | | | | | | | | | | |
|---|---|---|---|---|---|---|---|---|---|---|---|
| Case Selection | Organization | Cost Carrier | Basis of Computation | | Rehab Procedure | | | | | | |
| Time Range | 01.01.2000 | --- | 31.12.2000 | Kind of stay | ☑ Fully Inpatient ☑ Partly Inpatient ☑ Dialysis | | | | | | |
| Admission | | --- | | | Statistical case ☑ Case Statistic ☑ Special Case | | | | | | |
| Discharge | | --- | | | Budget status ☑ Resident ☑ Non-resident | | | | | | |
| Case Category | ☑ Patient ☑ Newborn w/DRG ☑ Newborn w/o DRG ☑ Acc. person w/ med. grnds. ☑ Acc. person w/o med. grnds. | | | | | | | | | | |

| Department/Station | | | | | | | | | | |
|---|---|---|---|---|---|---|---|---|---|---|
| Department | Station | Beds | Beginning status | External Admissions | Internal Admissions | Internal Releases | External Releases | Closing status | Treatment Days | |
| Department 05 | Station 02 | 12.0 | 0 | 2 | 5 | 7 | 0 | 0 | 2 | |
| Department 05 | Station 03 | 0.0 | 0 | 3 | 3 | 4 | 2 | 0 | 10 | |
| Department 05 | Station 02 | 0.0 | 0 | 1 | 17 | 18 | 0 | 0 | 6 | |
| Department 05 | Station 05 | 0.0 | 0 | 2 | 5 | 5 | 0 | 2 | 730 | |
| Department 05 | Station 07 | 4.0 | 6 | 104 | 73 | 57 | 119 | 7 | 2387 | |
| Department 05 | Station 09 | 31.0 | 15 | 756 | 219 | 171 | 796 | 23 | 10245 | |
| Department 05 | Station 10 | 6.0 | 4 | 75 | 486 | 510 | 52 | 3 | 1474 | |

SYSTEM AND METHOD FOR GENERATING EVALUATION DATA

This application claims priority to European Patent Application No EP 01724033, filed on Dec. 21, 2007.

The present invention relates to a system and a method for generating evaluation data from original data which are stored in a data base.

In a data base, which is normally disposed in a computer network with a plurality of computers connected to one another, original data can be stored which are generated by different applications provided on the computers and/or are received via interfaces and written into the data base. In general, both master and movement data are stored as original data in the data base. Master data are also called basic or reference data and are amended relatively rarely. They can, for example, describe an organisational structure. Movement data are amended e.g. with different processes within an organisation structure, and so generally more frequently than master data.

This type of data base is used for example in a computer network in a hospital environment. The applications running on the different computers of the computer network include for example a module for the medical care with which e.g. the administration of medicines, dressing materials etc. can be recorded, a module for the accounting with which e.g. the hospital's materials consumption can be recorded, or a module for logistics, i.e. in particular for the incoming and outgoing goods. The data base is in particular a relational data base which e.g. includes name, case and medicine tables etc.

Master data stored in the data base can display in particular the organisational structure of the hospital with its different units, departments, areas and ambulances etc. Movement data specify for example the addition or the release of a patient, the relocation of a patient from one unit to another unit, the administration of medicines to patients etc.

From the original data stored in the data base, by means of an evaluation program evaluation data can be generated which include key figures for the different processes within the hospital and so e.g. provide information about the respectively current number of patients being treated in the hospital. Depending on the type of key figure respectively desired, complicated calculations must be carried out in order to generate the evaluation data and the original data must be summarised and interpreted. This is sometimes very time-consuming.

The evaluation data generated are visualised e.g. by being displayed on a monitor in text form and/or in graphic from and/or shown on paper. It is also possible to display the evaluation data as a file. This can take place in particular in a so-called CSV or an XML format.

An evaluation of the original data stored in the data base is generally implemented when the evaluation data are requested by a user. The latter must then wait for the time required for the evaluation until the evaluation data generated by the evaluation are actually available and can be displayed. Under certain circumstances this can take an undesirably long time. Moreover, during the evaluation great demands are made of the calculating capacity of the computer which implements the evaluations and the whole computer network is heavily loaded due to the transfer of data between the data base and the computer associated with the evaluation.

After the user's request for evaluation data, the computer is therefore only available to the user for further work to a very limited extent. Moreover, the data transfer rate of the computer network slows down with the number of evaluations started.

It is the object of the invention to be able to make available evaluation data generated upon the basis of current original data quickly and reliably in a technically simple way.

This object is achieved according to the technical teaching of Claim 1 or 16.

The system according to the invention for generating evaluation data includes a data base for storing original data, a memory for storing an evaluation program for the evaluation of original data stored in the data base, and a control, an evaluation order for the evaluation of original data being generated upon the occurrence of a pre-specified event, it being checked by the control whether an evaluation order has been generated, and in the event of an evaluation order being present, the evaluation program stored in the memory being started dependently upon the evaluation order, and the evaluation program accessing original data stored in the data back dependently upon the evaluation order, and the evaluation data being generated from this. In order to access the data base and the memory the control is connected to the latter in a suitable way for the exchange of data.

With the corresponding method according to the invention, when a pre-specified event occurs, an evaluation order for the evaluation of original data is generated. Furthermore, it is checked whether an evaluation order has been generated, in the event of the presence of an evaluation order an evaluation program stored in a memory being started dependently upon the evaluation order which, dependently upon the evaluation order accesses original data stored in the data base and generates the evaluation data from this.

Upon the basis of the invention the occurrence of pre-specified events which result in a change to original data are continuously monitored so that the evaluation data can be continuously adapted to the changes to the original data—associated with the respective events—, i.e. updated as appropriate. Therefore, the evaluation data are available in up-dated form at all times. The advantage of this is that after requesting the evaluation data the user no longer needs to wait until the evaluation data have been established from the—at least partially amended—original data. A further advantage of the invention is also that high demands are no longer made of the calculating capacity of the computer which implements the evaluations and the transfer capacity of the computer network after the request for the evaluation data by the calculations for the evaluation data. Therefore, directly after requesting evaluation data the computer is immediately available to the user for further work with at the same time smaller demands made of the computer network.

In summary, it can be established that by means of the invention the evaluation data generated from the original data can be made available quickly and reliably in a technically simple way.

In one advantageous embodiment of the invention the control is designed such that the presence of an evaluation order is checked continuously, i.e. without any interruption. Within the context of the invention, "continuously" is to be understood as meaning that the presence of an evaluation order takes place at the shortest technically possible intervals of time. In this way it is possible for the evaluation program stored in the memory to be started practically immediately following generation of the evaluation order so that very rapid updating of the evaluation data can take place. In this way the up-dated evaluation data are already available a very short time following the occurrence of the pre-specified event, e.g. a change to original data.

Alternatively, the control can be configured such that the presence of an evaluation order takes place at longer settable intervals of time, e.g. every 10 seconds.

In a further advantageous embodiment of the invention the evaluation program has a number of different program parts for the evaluation of different original data, different types of evaluation order being generated dependently upon the pre-specified event and the control being designed such that it starts one of the program parts dependently upon the respectively generated type of evaluation order. With this embodiment the evaluation program includes a number of program parts, preferably so-called plug-ins, which are assigned to different types of evaluation order, i.e. a specific program part is only called up with the presence of a specific type of evaluation order. In connection with this one also says that this program part has "subscribed to" a particular type of evaluation order. With this embodiment of the invention the evaluation data can be generated particularly efficiently because upon the basis of the pre-specified event which has occurred only those evaluation data are newly calculated for which this is necessary in order to adapt them, i.e. update them, to the pre-specified event.

Within the context of the invention an evaluation order can also be called an "event" and a specific type of evaluation order an "event type".

In a further advantageous embodiment the control is designed such that one accesses original data stored in the data back dependently upon the respectively started program part. This guarantees more efficient generation of the evaluation data. It can be assumed here that when the pre-specified event occurs not all, but only certain original data relevant to the generation of the evaluation data have changed. It is advantageously established by the program part which original data are to be accessed and which evaluation data generated. Therefore, assignment of original data to the respective evaluation data to be generated in particular is established by the program part.

With a further development of the aforementioned embodiments, if pre-specified events occur two or more times in connection with a particular evaluation object, e.g. a case or patient, two or more evaluation orders are generated. The control is designed here such that one of the program parts is started for just one of these evaluation orders if the other evaluation orders would have resulted in the same program part starting. The status of the other orders issued is preferably set to "do not process" here.

The two or more evaluation orders can be of the same or of different types. It is essential with this embodiment that the evaluation orders—no matter of which type they are—would respectively start the same program part; which in this way would be implemented two or more times. The control is configured here such that it recognises this and only implements this program part once. This is illustrated by means of the following two examples.

EXAMPLE 1

If e.g. due to relocation of a case in the hospital which happens two or more times in close succession and which in this example constitutes the evaluation object, and which generates two or more evaluation orders of a specific type for the associated changes to output data, this is recognised by the control and the program part assigned to this type of evaluation order is started not for each relocation, i.e. two or more times, but just for one relocation.

EXAMPLE 2

If e.g. for a person, who constitutes the evaluation object here, successive pieces of information concerning name, sex, age etc. are entered or changed, and for this corresponding evaluation orders of different types are also generated, with changes to these data that take place two or more times the same program part respectively assigned to the evaluation orders of these types is only implemented once. The other evaluation orders belonging to the same evaluation object, i.e. to this patient, are deactivated so that no program parts of the evaluation program are implemented here.

By means of this further development of the invention it is possible for changes to the original data to be taken into consideration on the one hand as quickly and as often as necessary, and on the other hand as rarely as possible when establishing the evaluation data. The loading of the capacity of the system, i.e. of the computers involved, of the data base and of the computer network, is in this way kept small.

In one preferred embodiment of the invention the pre-specified event is a change to original data in the data base. Recognition of the change to original data preferably takes place automatically, for example by means of so-called data base triggers which continuously monitor changes to the original data inventory of the data base and in the event of a change to original data generate a corresponding evaluation order. The data base triggers are preferably implemented in the data base management system (DBMS) of the data base. Alternatively or in addition, the program module, for example an application, which stores and amends original data in the data base, can also generate corresponding analysis orders independently, with storage of the original data in the data base a corresponding evaluation order being generated at the same time. By recognising a change to original data and the subsequent generation of an evaluation order based upon this, the evaluation data affected by the change can advantageously be updated automatically and continuously.

Moreover, it is advantageous if the pre-specified event is reaching a pre-specified point in time or a pre-specified period. In this way the evaluation data can be kept up to date even better and more efficiently. In this case the evaluation order is generated over a controlled period. The evaluation data can therefore be adapted upon the basis of the continuing time. For this purpose it is not necessarily a requirement for the original data to be changed, added as new or deleted.

Preferably, the data base is additionally designed to store evaluation orders. The control is designed here so that it respectively selects one of the evaluation orders stored in the data base and, dependently upon the selected evaluation order starts the evaluation program stored in the memory which then accesses original data stored in the data base dependently upon the selected evaluation order. In this way generation of the evaluation data can be improved even further and be designed more efficiently.

Moreover, it is preferred if the evaluation orders are stored in the data base in a sequence and if the control is designed here so that it respectively selects one of the evaluation orders stored in the data base according to this sequence. In this way generation of the evaluation data can be produced flexibly and be adapted to different applications. By means of the sequence, for example, a priority of the evaluation orders can be specified. The evaluation orders are preferably stored and selected according to the "first in, first out" (FIFO) principle.

In a further advantageous embodiment of the invention the control is designed such that after a user request made by a user, the evaluation data generated are issued, the generation of the evaluation data coming before the user request in time. In this way the user always receives current analysis data which he can analyse or utilise as required. For example, he can view the current evaluation data graphically on a screen and/or a print-out.

Preferably the control is designed such that the evaluation data generated are stored in the data base. In this way in particular good accessibility of the evaluation data can be guaranteed.

In a further advantageous embodiment the system has an evaluation apparatus as a self-contained physical unit which comprises the memory and the control. The data base and the evaluation apparatus are connected to one another here for the exchange of data. In this way the different functions, i.e. in particular the evaluation and the storage of the original data can be arranged optimally in the different physical units.

In one particularly preferred embodiment of the invention a computer network is provided which contains a number of computer devices which are connected to one another and to the data base for the exchange of data. Different applications can be installed in the computer devices which store original data in the data base. The integration of the data base into the computer network offers a particularly great abundance of possibilities for use. In the case of an evaluation apparatus as an independent physical unit these can advantageously also be linked to the computer network.

Preferably the system according to the invention is designed as a hospital information system (HIS, CIS), the original data comprising a plurality of master and/or movement data which are generated in a hospital by medical and/or logistic and/or administrative processes and which comprise evaluation data key figures for these processes in the hospital generated from the original data. The processes implemented in a hospital are particularly complex, and so use of the present invention is particularly advantageous in order to always have updated evaluation data available despite constant changes to a plurality of original data.

A further particular advantage of the invention is that the system and method can use events, i.e. evaluation orders, which are primarily required and generated for the purpose of communication with other systems such as e.g. SAP. With the system and method according to the invention in this way only one corresponding use of these events needs to be configured. For this purpose the control is adapted in a way such that dependently upon the event type a corresponding program part which must if applicable still be established is called up which up-dates evaluation data by accessing original data. Therefore, e.g. the incorporation of a patient into a hospital information system is a typical event with which for the purpose of communication an event is already generated. This event already generated can now be used at the same time for the generation of evaluation data which preferably include key figures for these processes in the hospital.

Figure 2:
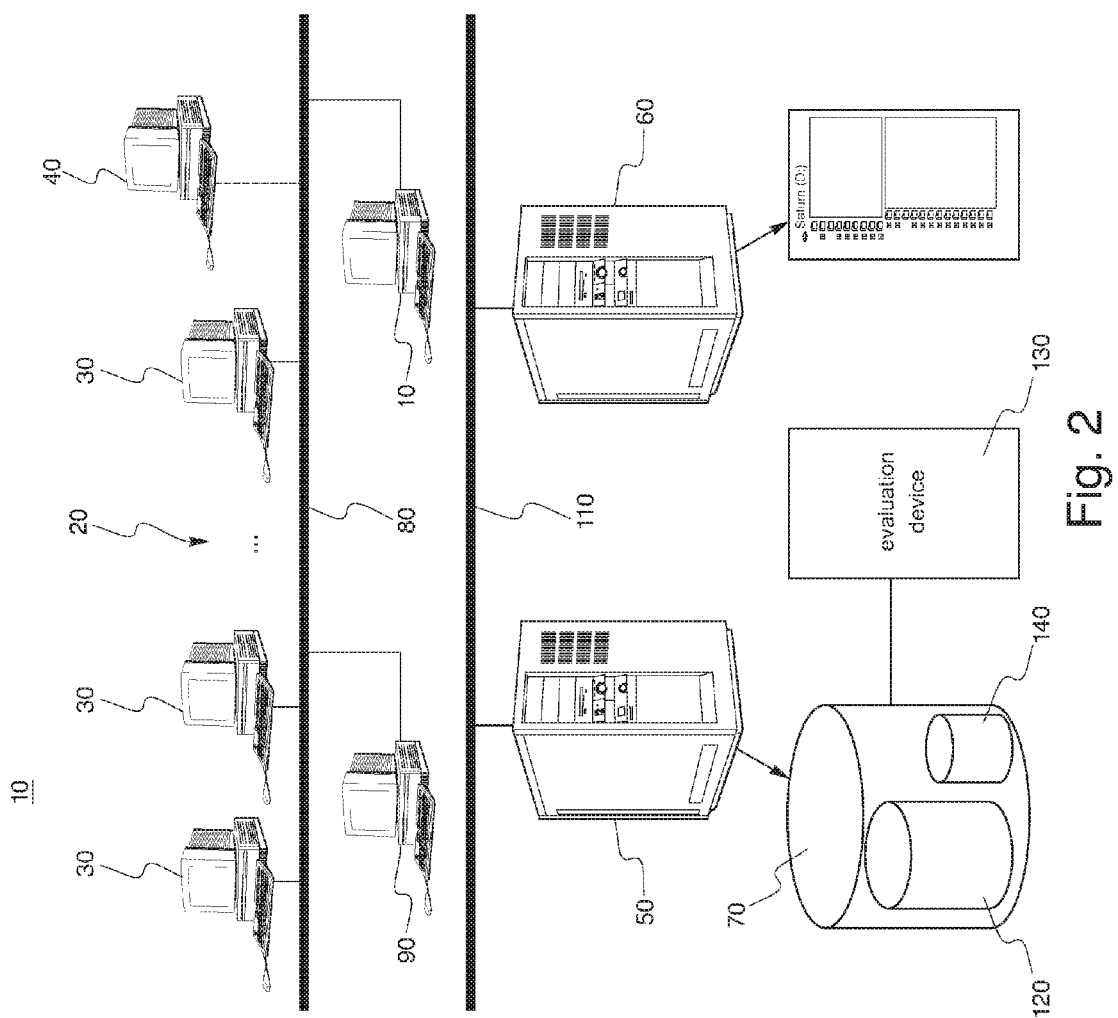
Figure 3:
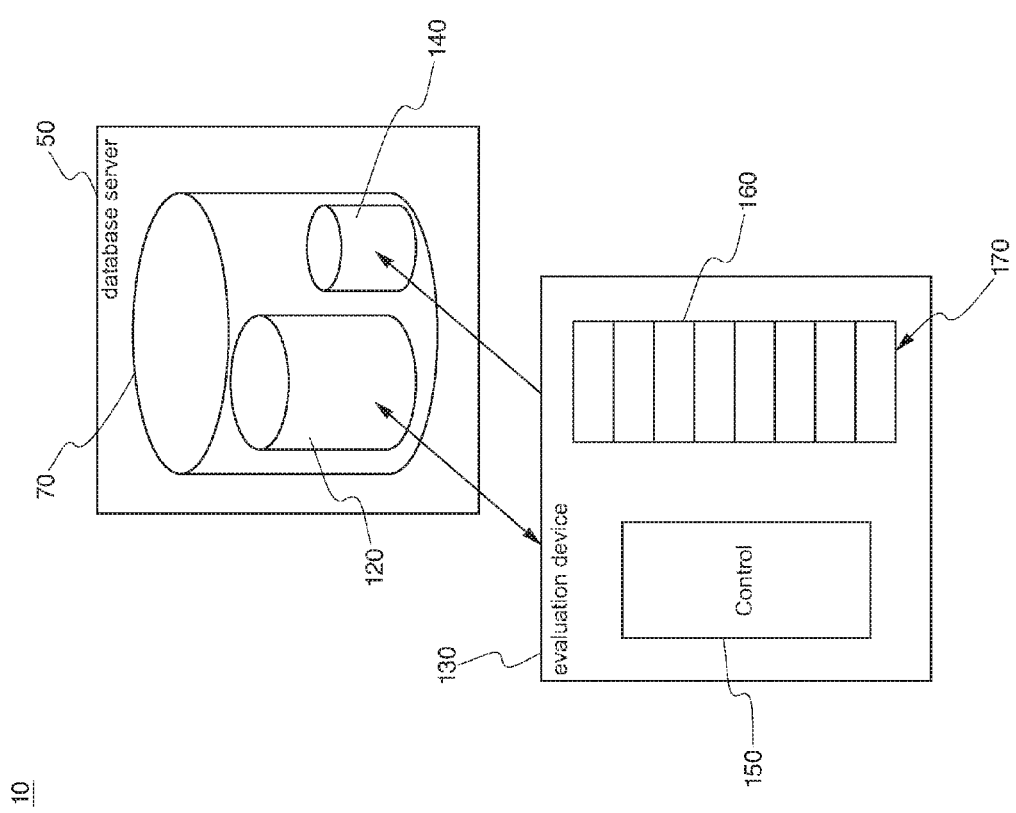
Figure 4:
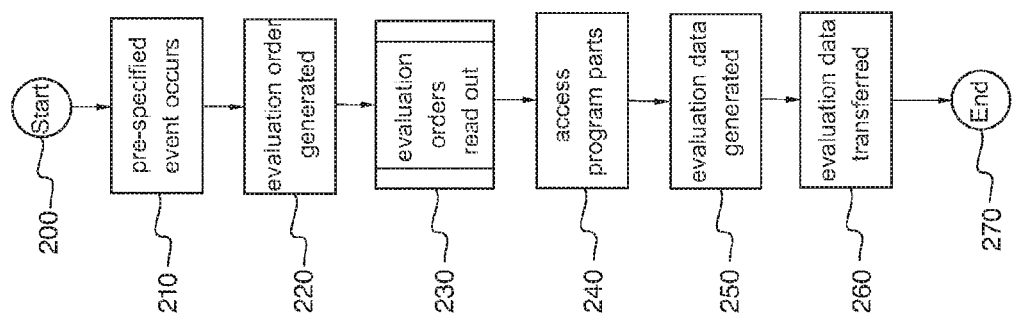

Further advantages of the invention are given by the following description of exemplary embodiments, reference being made to the attached drawings. These show as follows:

FIG. 1 a diagrammatic illustration of a first exemplary embodiment of a system according to the invention with a computer network with which different client computers can directly access a data base and a file server, FIG. 2 a diagrammatic illustration of a second exemplary embodiment of a system according to the invention with a computer network, with which different client computers can access terminal servers which in turn are connected to a data base and a file server, FIG. 3 a diagrammatic illustration of an evaluation device connected to a data base server, the data base server and the evaluation device being component parts of the systems according to the invention according to the first and the second exemplary embodiment, FIG. 4 a flow chart of an exemplary embodiment of the method according to the invention, FIGS. 5A, B an example comparing a method according to the prior art and a method according to the invention with which a number of overnight stays of patients in a hospital within a year is respectively determined, and FIGS. 6A-F an example of application of the method according to the invention with which evaluation data are provided which in a hospital administration system according to the invention include information about possible additional fees that can be charged.

In the following, unless specified to the contrary, the same reference numbers are used for the same elements or those with the same effect.

FIG. 1 shows a diagrammatic illustration of a first exemplary embodiment of the system 10 according to the invention. The system 10 in this example is a hospital administration system which is installed for the administration and implementation of a plurality of tasks in a hospital.

The system 10 comprises a computer network 20 with a plurality of different computers 30 accommodated within the hospital and a computer 40 integrated from outside of the hospital into the network 20 for example by means of a so-called Virtual Private Network (VPN). The computers 30 and 40 are clients of a client server architecture.

The system 10 further includes a central data base server 50 and a central file server 60. The data base server 50 includes a data base 70 which here can be for example a data base produced by the company Oracle. Different applications used in the hospital for the administration are installed on the file server 60. Alternatively, the applications can also be installed directly on the computers 30 and 40.

The computers 30, 40, the data base server 50 and the file server 60 are respectively connected to a TCP/IP based network 80 which here is a so-called Local Area Network (LAN). Therefore, the computers 30, 40 can access the data base server 50 and the file server 60 directly.

FIG. 2 shows a diagrammatic illustration of a second exemplary embodiment of the system 10 according to the invention. The system 10 of the second exemplary embodiment largely corresponds to the system 10 of the first exemplary embodiment which was described by means of FIG. 1.

Unlike the system 10 according to the first exemplary embodiment, the computers 30, 40 are not connected directly to the data base server 50 and to the file server 60 here. Rather, the system 10 includes a number of terminal servers of which two terminal servers 90 and 100 are illustrated representatively in FIG. 2.

By means of the terminal servers 90, 100 the LAN 80, to which the computers 30, 40 are connected, is connected to a further LAN 110 as a TCP/IP-based network. The data base server 50 and the file server 60 are in turn connected to the LAN 110. Therefore, in this exemplary embodiment the computers 30, 40, as clients, do not access the data base server 50 and the file server 60 directly, but via the terminal servers 90, 100.

In the following, unless noted to the contrary, the system 10 and its mode of operation are described both for the first and for the second exemplary embodiment.

The applications can for example be copied or installed onto the different computers 30, 40 at the start of a main application with the system 10 according to the first exemplary embodiment and onto the terminal servers 90, 100 with the system 10 according to the second exemplary embodiment.

For the system 10 it is the case that by using the applications installed on the file server 60 the clients 30, 40 can generate original data which they store centrally in a data base region 120 of the data base 70. The original data generated are master and movement data which in particular are input by users of the system 10.

Evaluations are to be prepared from the original data stored in the data base region 120. Depending on the type and information content of these evaluations the original data must under certain circumstances be summarised and interpreted in complicated calculation steps. By means of the evaluations evaluation data are generated from the original data.

In the present example of use of the system in a hospital the evaluation data are preferably so-called statistical data which provide the user with information in the form of specific key figures for different procedures in the hospital, such as e.g. medical care, accounting or logistics.

In order to evaluate the stored original data and to generate the evaluation data the system 10 has an evaluation device 130 which constitutes a self-contained physical unit. The evaluation device 130 is connected to the data base server 50 for the exchange of data. The evaluation data generated by the evaluation device 130 can advantageously have a particular data model which is separate from that of the original data. The evaluation data are stored in a particular data base region 140 in the data base 70.

The evaluation data stored in the region 140 can be called up by a user, for example in order to process and/or evaluate them further, and in particular in order to visualise them. For this purpose the user can access the data base server 50 and the evaluation data stored in its region 140 by means of one of the computers 30, 40. The visualisations of the evaluation data can for example be displayed on a monitor of the computers 30, 40 or be printed onto paper. It is also possible to issue the evaluation data in file form, for example in a CSV or XML format.

FIG. 3 shows a somewhat more detailed diagrammatic illustration of the evaluation device 130 which is connected to the data base server 50. The evaluation device 130 includes a control 150 for controlling the evaluation device 130 and in particular for controlling the evaluation of the original data stored in the data base region 120 and the generation of the evaluation data. The evaluation device 130 further includes a memory 160 in which an evaluation program is stored with which the original data are evaluated. The evaluation program is sub-divided into a number of program parts 170 which can also be called plug-ins. The program parts 170 can in principle be provided in different programming languages. In the present case the program parts 170 are programmed in the Java programming language.

FIG. 4 shows a flow chart of an exemplary embodiment of a method according to the invention. The method according to the invention starts with a method step 200.

Occurrence of a pre-specified event is represented by a step 210. This type of pre-specified event can be a change to original data in the data base 70 or reaching a pre-specified point in time or a pre-specified period. In the region 120 of the data base 70 both master and movement data can change here.

This type of change to master data can take place in the hospital environment of the exemplary embodiments described here if for a specialist department of the hospital e.g. the intensive care unit, an indicator "release day from the hospital" is changed from the status "do not count" to the status "count". This means that as evaluation data for all patient cases which have been released from this specialist department the respective release is to be subsequently determined and changed accordingly.

There is a change to movement data e.g. when a patient's stay in a specialist department is subsequently extended or shortened. In this case the evaluation data for the stay of this patient case are to be established once again. If the stay has been shortened, excess days taken into account must be deleted. If the stay has been extended additional days must correspondingly be determined and taken into account.

A further example of a change to original data is the new entry for a patient's stay. In this case the evaluation data are to be changed if original data regarding the receipt and the stay in the specialist department, e.g. a diagnosis, are added for the first time. There is also a change to the original data if for example a patient's stay is cancelled. Under certain circumstances all entries for this patient case must be deleted from the data base region 140 or be marked as invalid.

Furthermore, changes to the original data also occur when a patient's stay in the hospital comes to an end. Therefore, in the data base region 140 information on the patient's release must be noted. Any excess days taken into account must be correspondingly deleted or be marked as invalid.

An example of reaching a pre-specified point in time or a pre-specified period is if after a point in time for generating original data a new day has occurred. Evaluation data for the stay of all patient cases which continue to be in the hospital when the day changes are to be established once again. The duration of the stay of the different patient cases in the hospital is to be increased by one day. In the latter case a change to the original day must not necessarily also have occurred.

A plurality of further pre-specified events which can lead to generation of evaluation data is possible.

On the data base 70 so-called data base triggers are established by means of which changes to the original data inventory of the data base 70 are continuously monitored and recorded and then in a step 220 a corresponding evaluation order for the evaluation of original data is generated.

This type of evaluation order can also be called an "event". In this example the evaluation order is stored in a special table for evaluation orders.

Alternatively or in addition in step 220 an event, i.e. an evaluation order, can also be generated in step 220 by means of a program module, for example one of the applications installed on the file server 60 which implements certain predefined operations and be stored in the special table provided for this purpose. An example of this is the new receipt of a patient into the hospital. Here among other things the name, the address and a diagnosis must be recorded. Therefore from this new recording of the patient a number of tables of the data base 70 can be concerned with original data.

The special table for evaluation orders is preferably stored in a table located in the data base 70.

Preferably a special type of evaluation order is generated by the data base or the program module dependently upon the type of the event which has respectively occurred. The type of evaluation order is therefore assigned to one or more particular pre-specified events.

A number of evaluation orders can be stored in the table in a particular sequence. This sequence is determined for example according to the type to which the respective evaluation orders belong, a pre-specified priority and/or according to the principle of "first in, first out" (FIFO).

In a further step 230 of the method according to FIG. 4 the evaluation orders stored in the special table are read out from the table according to the, if applicable, pre-specified sequence of the control 150.

In a subsequent step 240 the control 150 accesses one of the program parts 170 dependently upon the evaluation order, in particular dependently upon the type of evaluation order, said program part 170 being implemented in a subsequent step 250 in which the evaluation data are generated. The program parts 170 stored in the memory 160 are therefore assigned to the evaluation orders, in particular to the types of evaluation order. By means of the respective program part 170 selected and implemented by the control device 150 the evaluation data which are generated by means of the respective program part 170 are established.

In a subsequent step 260 the evaluation data generated are then transferred to the data base region 140 and stored here. If appropriate, "dated" evaluation data already present in the region 140 are deleted or overwritten by the new evaluation data. In a step 270 the method according to the invention is ended.

With the present system and method according to the invention the evaluation data are therefore "event-based" updated, i.e. the evaluation data are updated dependently upon the occurrence of a particular event and the associated generation of a particular event, i.e. an evaluation order.

It is in principle possible according to the invention to dispense with allocation of a type to the evaluation order. In this case the evaluation order is assigned on the one hand to the pre-specified event recorded and on the other hand to one or more of the program parts 170.

According to the invention the evaluation data are regularly generated when a pre-determined event is recorded. The evaluation data are generated by generation of the evaluation order and the appropriate assignment and selection of the program parts 170. It can therefore advantageously be ensured that constantly current evaluation data are stored in the region 140 of the data base 70. Therefore, a user who calls up evaluation data from the region 140 constantly receives current evaluation data. It is not necessary when evaluation data are called up by the user for these first of all to be re-generated in up-to-date form. The loading of the control 150 due to generation of the evaluation data can therefore largely be stretched out over a longer period of time. Therefore, isolated heavy loading of the control 150, as is necessary when re-generating the evaluation data upon a user request, is avoided.

According to the invention it is further guaranteed that only those evaluation data are generated for which it is necessary due to the respectively recorded pre-specified event for them to be kept up-to-date.

By means of the pre-generation of evaluation data according to the invention the control device 150 or one of the computers 30, 40 on which current evaluation of the original data is required, is very quickly available to the user again for other purposes.

In addition, FIGS. 5A and 5B show an example comparing a method according to the prior art (FIG. 5A) and a method according to the invention (FIG. 5B). With the comparative example, according to both methods a number of patients' overnight stays in a hospital within a year, here the year 2000, is respectively determined.

Figure 5A:
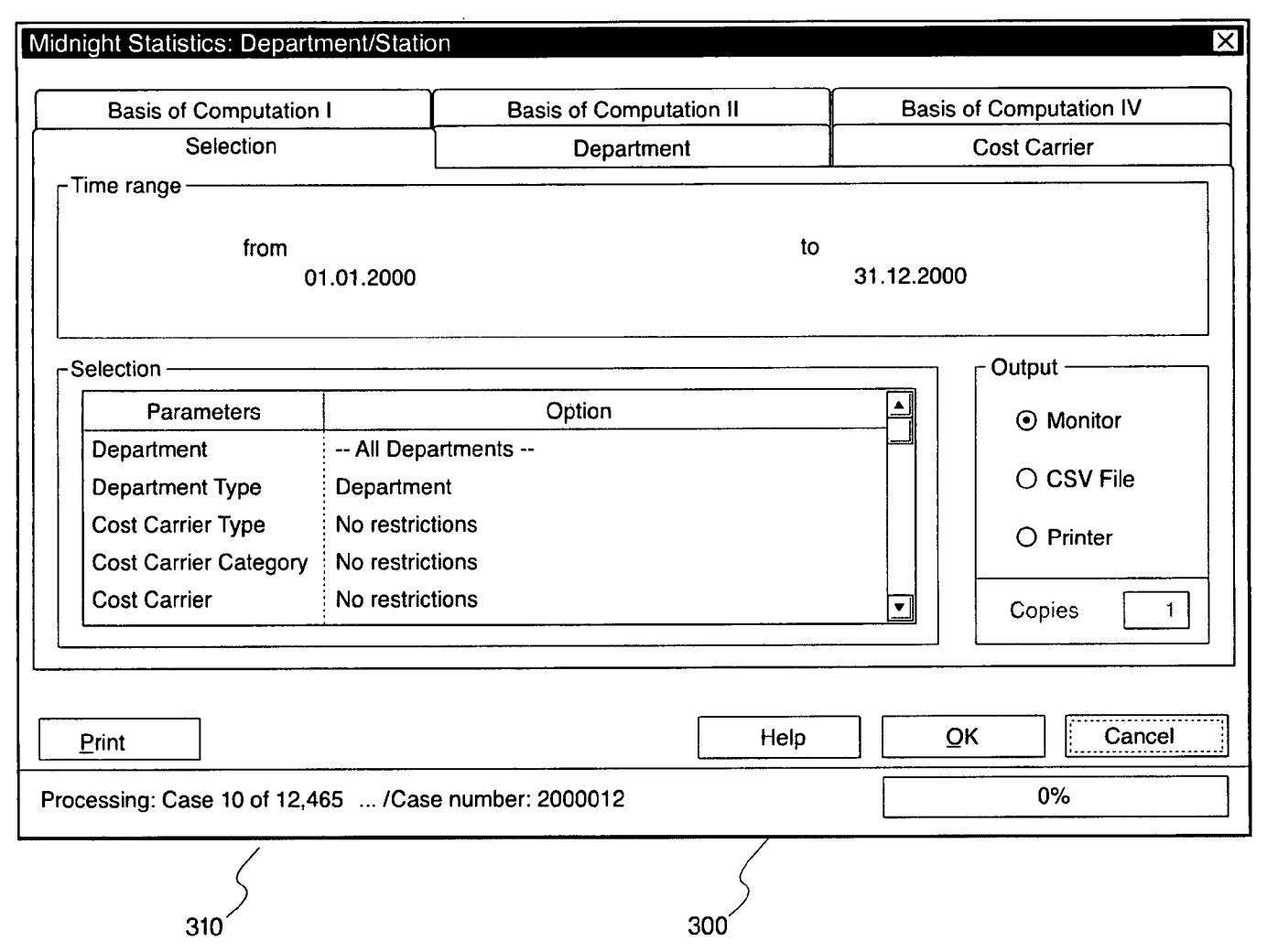

FIG. 5A shows a mask 300 which is displayed to the user on his monitor. In this procedure according to the prior art following the user's request all of the patient cases and the evaluation data required are re-calculated one after the other. In particular here these are the duration of the stay in different specialist departments and unit combinations, relocation information, information regarding, if applicable, from which hospital the respective patent has come or to where he has been relocated, information regarding granting of leave to the respective patient, etc.

The respective currently recorded patient, called a "case", is displayed in the mask in a field 310 in which a counter counts up the patient cases individually. In the example according to FIG. 5A this is at present patient case 10 of 12465 patient cases. In the present example according to FIG. 5A the system 10 requires approx. 5 minutes and 30 seconds until the complete result has been generated and the desired evaluation data are available to the user.

FIG. 5B shows a mask 320 in which the desired evaluation data are already displayed in a field 330 after approx. 30 seconds. This is possible since the current evaluation data are already stored in the data base region 140. Therefore, the desired evaluation data must only be selected from the data base 70 and transferred to the user's computer. A complex calculation of the desired evaluation data is no longer required.

FIGS. 6A-F show an application example of the present invention. With this application example evaluation data are provided which in the hospital administration system 10 according to the invention include information about possible additional fees chargeable. Additional fees are services which can be charged for by the hospital in addition to other "normal" services with a patient case. In Germany additional fees can be charged for example parallel to a case-based lump sum.

In the present example the user would like to know at the time of the stay of a plurality of patient cases in the hospital which potential additional charges these patient cases might bring about. Instead of re-calculating evaluation data with this information upon a corresponding request, according to the invention the procedure described above is implemented by means of evaluation orders. The potential additional charges established as evaluation data are stored in a table with the name ZEPOT. Additional charges are established in principle from different pieces of information. These include e.g. stored operation codes (OPS), age of the patient case, date of receipt etc. OPS are procedure codes which are based upon the German adaptation of the international WHO-ICPM (World Health Organisation-international Classification of Procedures in Medicine) catalogue. The program sequence resulting from the recording of an OPS is described and illustrated.

The starting point for the application example according to FIGS. 6A-F is the recording of an OPS in the system 10 with regard to the patient case with a case number 2751395.

Figure 6A:
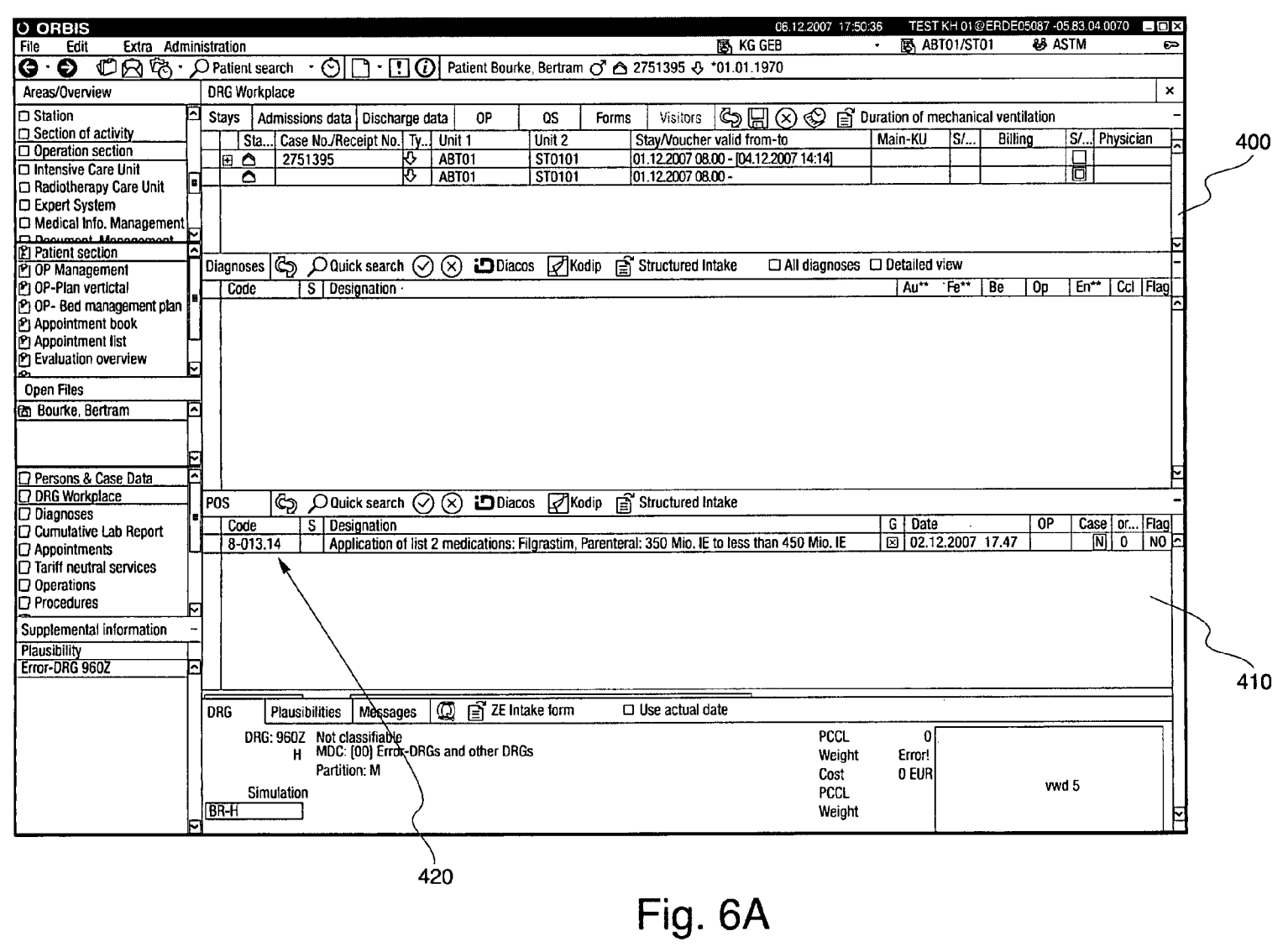

FIG. 6A shows a mask 400 which is displayed on a monitor during the course of the method according to the invention and which can be used by the user. First of all an OPS is recorded as changed original data by the control 150. This OPS is displayed to the user in a field 410 and is provided here with reference number 420. For the recording of the OPS there are in principle a number of possibilities such as e.g. by means of a quantity calculator, manual input or transfer via an external interface.

Figure 6B:
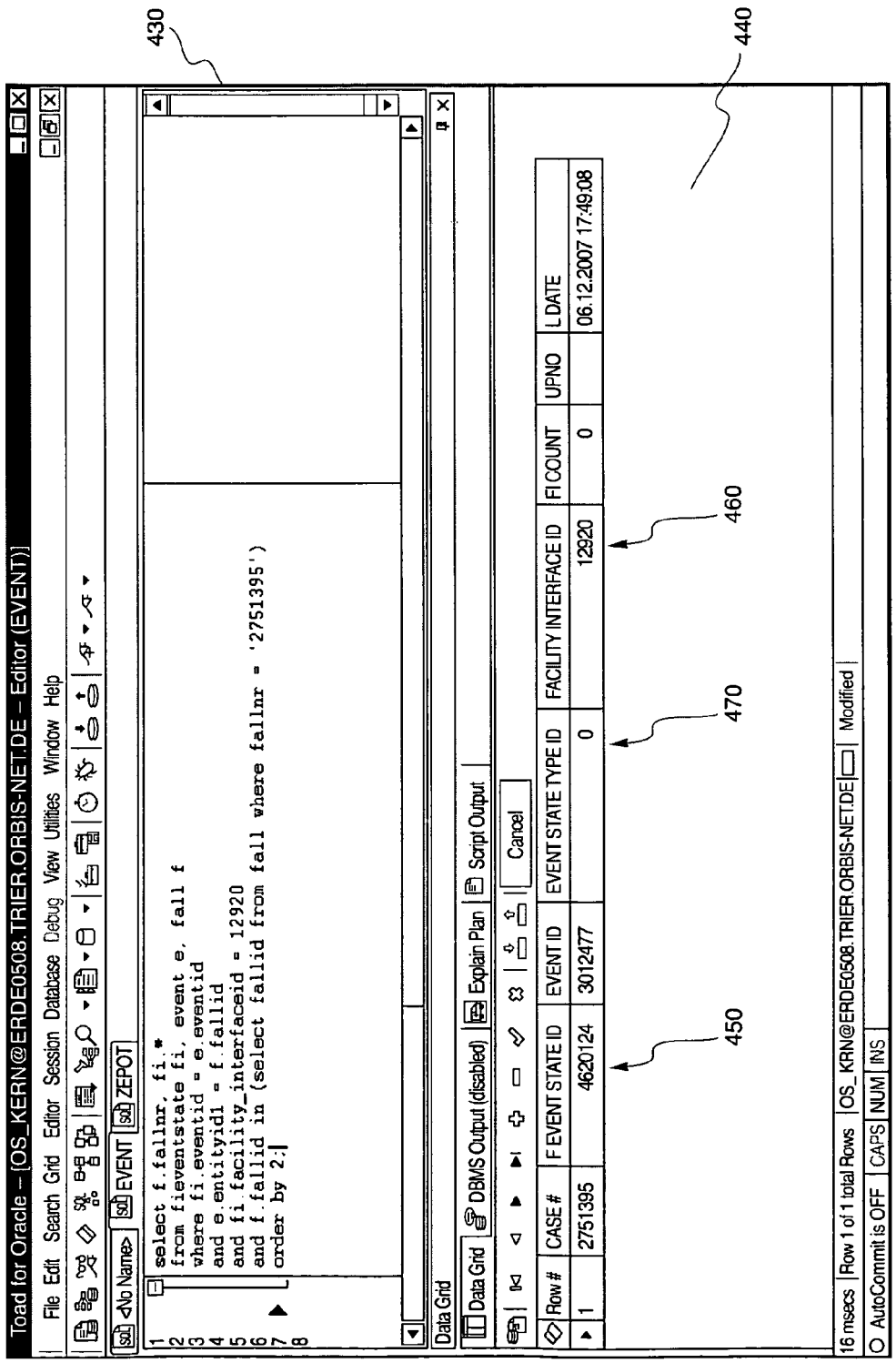
Figure 6C:
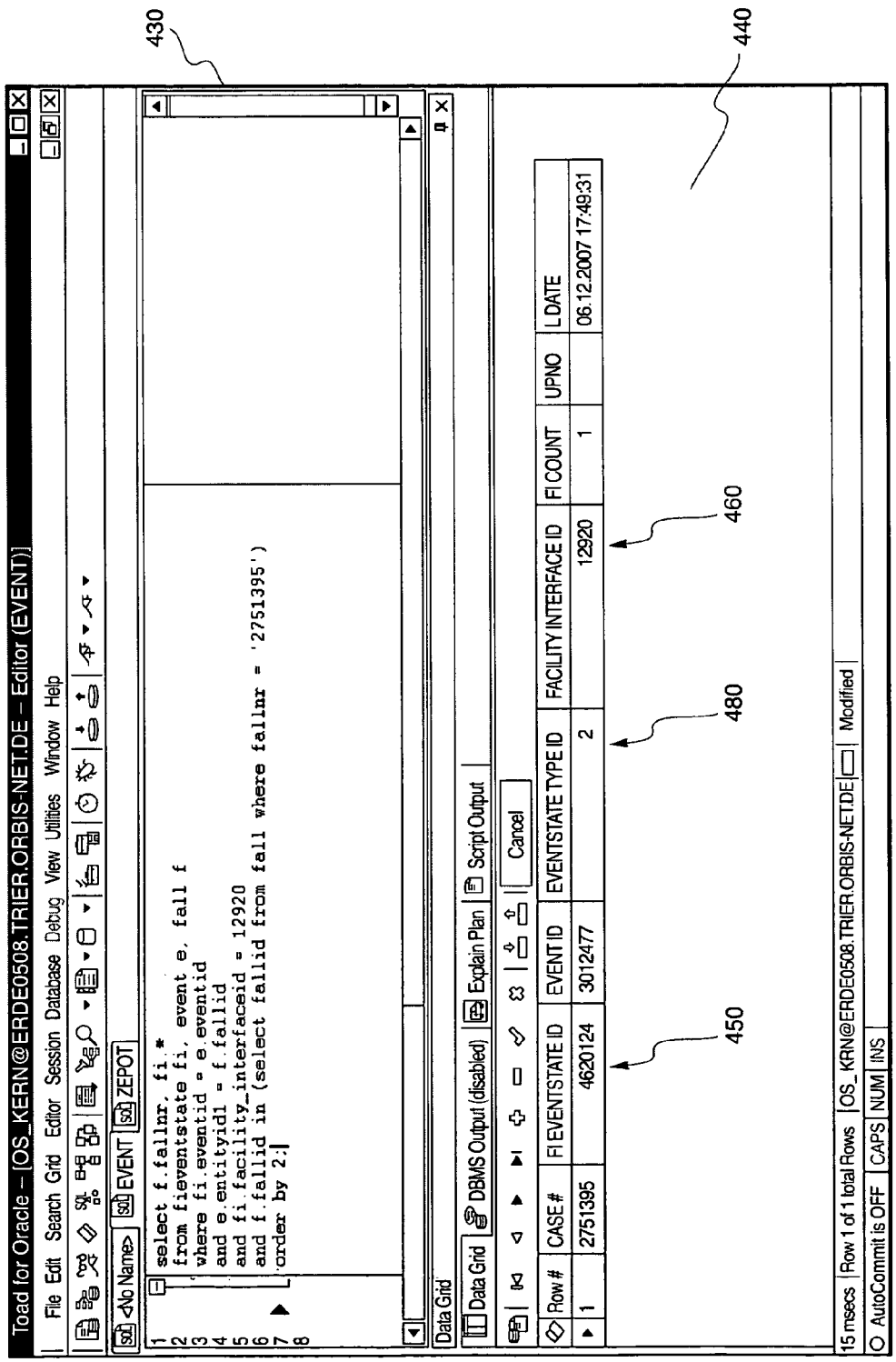

By recording and encoding the OPS an evaluation order is triggered and generated. This initially happens independently of whether the OPS is relevant to determination of the additional fee or not. FIG. 6B shows a mask 430 of a table FIEVENTSTATE which is a special table for the storage of evaluation orders. The mask 430 has a field 440 with an entry 450. The entry 450 is an evaluation order with a FIEVENTSTATEID 4620124. The table FIEVENTSTATE additionally specifies whether the evaluation order was written for a specific program part 170 of the evaluation program in the table FIEVENTSTATE. The program part 170 which is concerned with the generation of evaluation data with the information about the potential additional fees has the ID 12920 here. This is shown in the table FIEVENTSTATE in the column FACILITY_INTERFACEID and is provided with reference number 460. In the column EVENTSTATETYPEID of the field 440 one finds the entry 0. This is provided here with reference number 470 and means that the entry 450 was still being processed by the evaluation device 130. The associated program part 170 has not yet been called up.

FIG. 6C once again shows the mask 430, however in the column EVENSTATETYPEID of the field 440 there being the entry 2. This is identified by reference number 480 and means that the evaluation order was now being processed under the entry 450. The evaluation data were generated by means of the assigned program part 170 provided with the ID 12920.

Figure 6D:
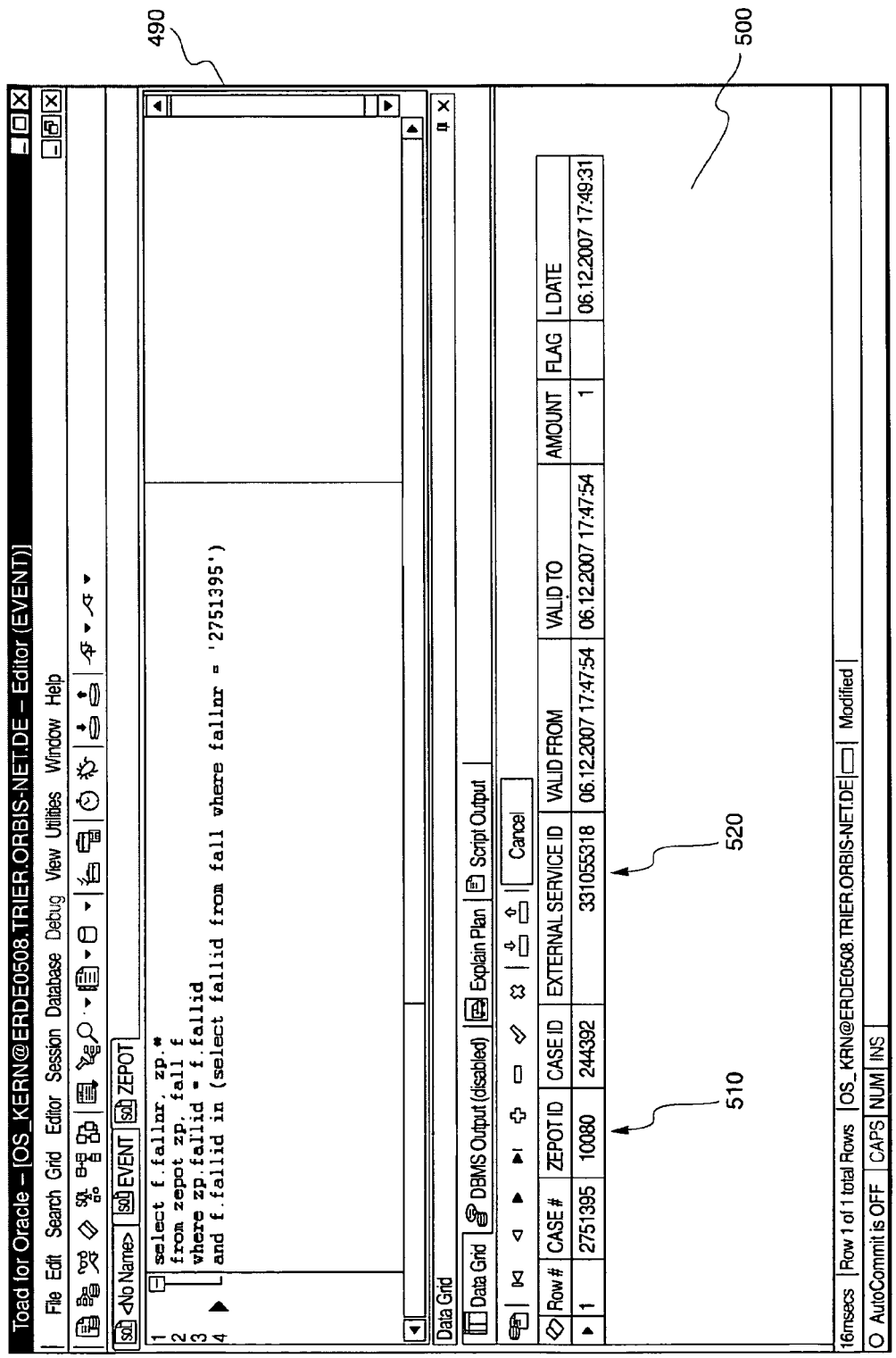

FIG. 6D shows a mask 490 in which in one field 500 a table ZEPOT is shown. Since the OPS was chosen here so that it leads to an additional fee, the table ZEPOT includes an entry 510 with an additional fee with regard to the patient case being considered. In this respect the entry 510 constitutes evaluation data. The additional fee is concealed behind an entry ZEPOT.EXTERNALSERVICEID which is provided with reference number 520. This code 520 leads as a foreign code to the actual text of the chargeable service.

Figure 6E:
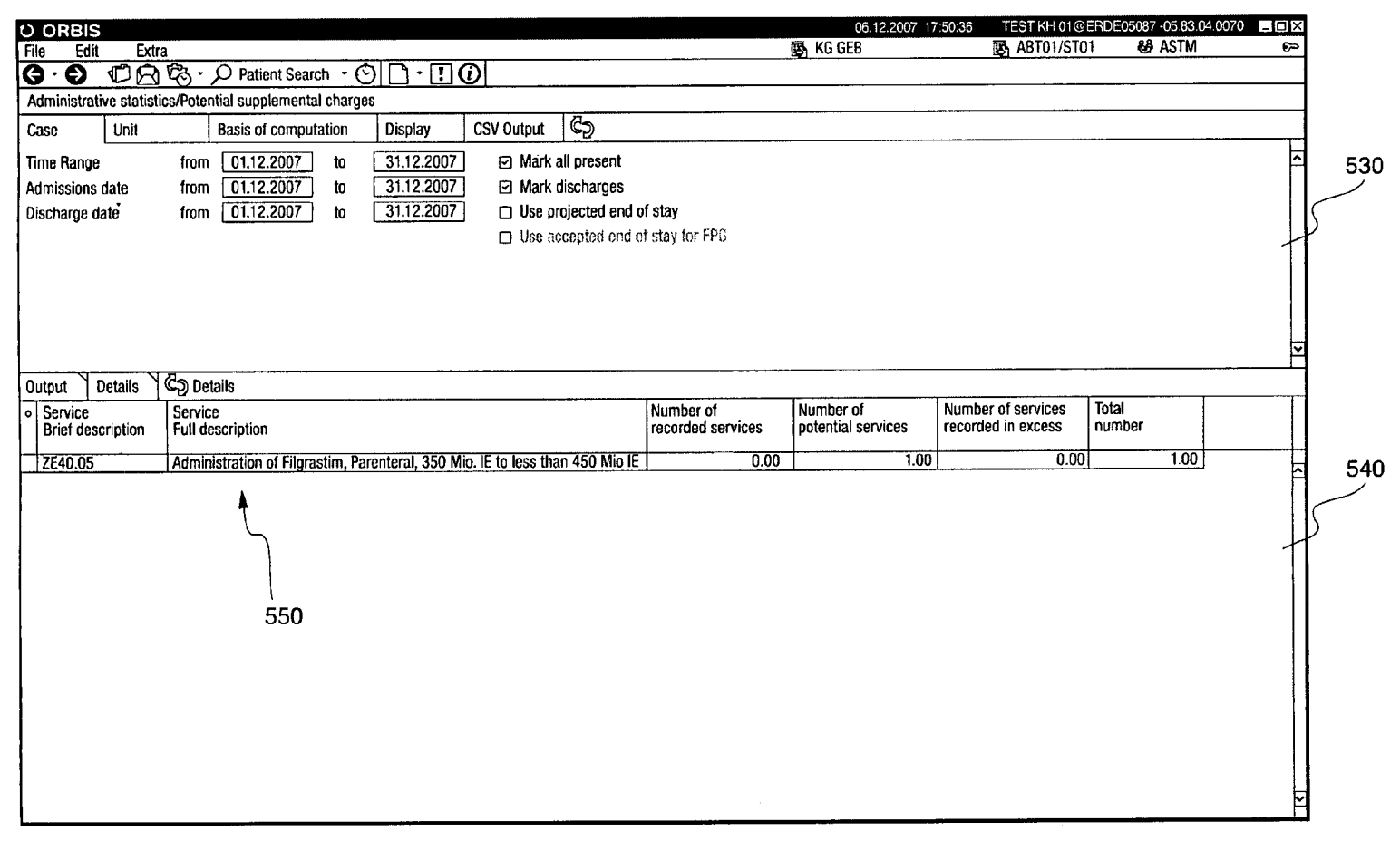

FIG. 6E shows a mask 530 which is displayed on the monitor after the processing of a request for the system 10 to display the potential additional fees. In a field 540 the mask 530 includes in text form the whole list concerning the additional fee that can be charged. In the present example this is a detail 550 with which an additional fee can be charged for administration of filgrastim.

Figure 6F:
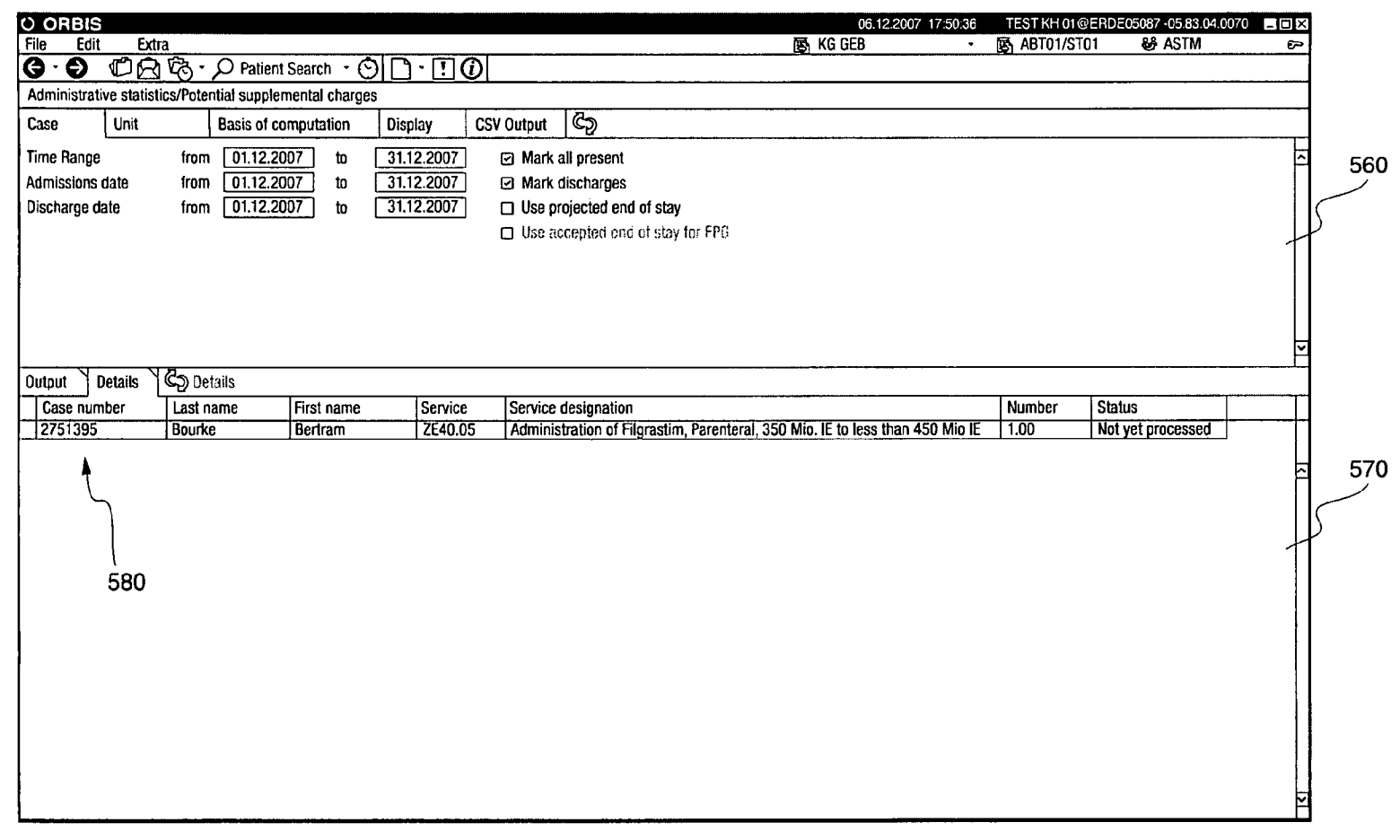

FIG. 6F shows a mask 560 which is also displayed on the monitor after the processing of a request for the system 10 to display the potential additional fees. In one field 570 the mask 560 includes in text form the overall result already displayed in the field 540, here however in relation to the patient case with the case number 2751395 already specified above. This is clarified in FIG. 6F by a reference number 580.

The present invention has been described in the exemplary embodiments portrayed here and in examples by means of a hospital environment. However, it is also possible to use the invention in another field of application.

The invention claimed is:

1. A system for generating evaluation data with a data base for storing original data, a memory for storing an evaluation program for the evaluation of the original data stored in the data base and a control, wherein the system:

generates an evaluation order automatically for evaluating the original data, the evaluation order being generated upon the occurrence of a change to the original data in the data base, wherein the original data characterizes medical, logistic or administrative processes in a hospital environment and the change to the original data comprises a relocation of a case within a hospital, changing patient information concerning a name, age, gender or address of a patient, changing a status of a release date from "do not count" to "count", changing hospital stay data by beginning, ending, extending, shortening, or cancelling a hospital stay of a patient, or an addition of a stored operation code, the control checks whether an evaluation order has been generated, and in the event of an evaluation order being present, the evaluation program stored in the memory is started in dependence upon the evaluation order, wherein the evaluation program has a number of different program parts for the evaluation of different original data, wherein different types of evaluation orders are generated depending upon the change to the original data and one of the program parts is started depending upon the respectively generated type of evaluation order and wherein if changes to the original data occur two or more times in connection with a particular evaluation object, two or more evaluation orders are generated and the control is designed to start one of the program parts for just one of these evaluation orders if the other evaluation orders would have resulted in the same program part starting, the evaluation program accesses the changed original data stored in the data base depending upon the evaluation order, and the evaluation data are generated by the evaluation program from the changed original data, the evaluation data being key figures pertaining to the medical, logistic or administrative processes, the evaluation data being derived from the changed original data.

2. The system according to claim 1, wherein the control continuously checks for a presence of an evaluation order and the evaluation program stored in the memory is started directly after generation of the evaluation order.

3. The system according to claim 1, wherein the original data stored in the data base is accessed depending upon the started program part.

4. The system according to claim 1, wherein the data base is additionally designed to store evaluation orders and the control is designed to respectively select one of the evaluation orders stored in the data base and, depending upon the selected evaluation order, the evaluation program stored in the memory is started with the evaluation program accessing original data stored in the data base depending upon the evaluation order.

5. The system according to claim 4, wherein the evaluation orders are stored in the data base in a sequence and the control respectively selects one of the evaluation orders stored in the data base according to this sequence.

6. The system according to claim 1, wherein the control is designed such that after a user request made by a user, the evaluation data generated are issued, the generation of the evaluation data occurring before the user request.

7. The system according to claim 1, wherein the control is designed such that the evaluation data generated are stored in the data base.

8. The system according to claim 1, further comprising an evaluation apparatus which forms a self-contained physical unit and comprises the memory and the control, the data base and the evaluation apparatus being connected to one another for the exchange of data.

9. The system according to claim 1, further comprising a computer network that contains a number of computer devices that are connected to one another and to the data base for the exchange of data.

10. The system according to claim 1, which is designed as a hospital information system, wherein the original data comprises a plurality of master or movement data which are generated in a hospital by medical or logistic or administrative processes, and the evaluation data are generated from the original data comprising key figures for these processes in the hospital.

11. The system according to claim 1, wherein at least one evaluation order serves the purpose of the exchange of data from the system with another system.

12. The system according to claim 1, wherein the original data includes a name, age, gender or address of a person.

13. The system according to claim 1, wherein the original data includes a diagnosis of a patient and the evaluation data comprises information about possible additional fees chargeable.

14. The system according to claim 1, wherein the original data includes a date of release from a hospital of a patient and the evaluation data comprises a duration of a hospital stay of a patient.

15. The system according to claim 14, wherein the evaluation data comprises a total number of overnight stays of a patient in a hospital during a year.

16. The system according to claim 1, wherein the evaluation data comprises statistical data.

17. A method of generating evaluation data, comprising:
storing original data in a data base, wherein the original data characterizes medical, logistic or administrative processes in a hospital environment,
automatically generating an evaluation order for the evaluation of original data upon the occurrence of a change to the original data in the data base or reaching a pre-specified point in time or after expiration of a pre-specified period wherein the change to the original data comprises a relocation of a case within a hospital, changing patient information concerning a name, age, gender or address of a patient, changing a status of a release date from "do not count" to "count", changing hospital stay data by beginning, ending, extending, shortening, or cancelling a hospital stay of a patient, or an addition of a stored operation code,
checking whether an evaluation order has been generated, and in the event of an evaluation order being present, starting an evaluation program stored in a memory depending upon the evaluation order, the evaluation program having a number of different program parts for the evaluation of different original data,
the evaluation program accessing changed original data stored in the data base depending upon the evaluation order, and
the evaluation program generating the evaluation data from the changed original data, the evaluation data being key figures pertaining to the medical, logistic or administrative processes, the evaluation data being derived from the original data, and
if changes to the original data occur two or more times in connection with a particular evaluation object, generating two or more evaluation orders and starting one of the program parts for just one of these evaluation orders if the other evaluation orders would have resulted in the same program part starting.

18. A method for a hospital information system that processes original data comprising a plurality of master or movement data which are generated in a hospital by medical or logistic or administrative processes and generates evaluation data that are generated from the original data comprising key figures for these processes in the hospital, the system comprising a data base for storing the original data, a memory for storing an evaluation program for the evaluation of the original data stored in the data base, and a control, the method comprising:
generating an evaluation order for evaluating the original data, the evaluation order being automatically generated upon the occurrence of a change to the original data in the data base, wherein the original data includes a diagnosis of a patient and wherein different types of evaluation orders are generated depending on the change to the original data in the data base, and wherein the change to the original data comprises a relocation of a case within a hospital, changing patient information concerning a name, age, gender or address of a patient, changing a status of a release date from "do not count" to "count", changing hospital stay data by beginning, ending, extending, shortening, or cancelling a hospital stay of a patient, or an addition of a stored operation code,
the control checking whether an evaluation order has been generated, and in the event of an evaluation order being present, starting the evaluation program in the memory in dependence upon the evaluation order wherein the evaluation program has a number of different program parts for the evaluation of different original data and one of the program parts is started depending upon the respectively generated type of evaluation order, and
the evaluation program accessing the original data stored in the data base depending upon the started program part,
the evaluation program generating the evaluation data from accessed changed original data and storing the evaluation data in the database, the evaluation data being statistical data pertaining to the medical, logistic or administrative processes, the evaluation data being derived from the changed original data,
in response to a user request made by a user, the evaluation data are issued, the generation of the evaluation data occurring before the user request, and
if the occurrence of a change to the original data in the data base occurs two or more times in connection with a particular evaluation object, generating two or more evaluation orders and the control starting one of the program parts for just one of these evaluation orders if the other evaluation orders would have resulted in the same program part starting.

19. The method according to claim 18, further comprising the control continuously checking for a presence of an evaluation order and the evaluation program stored in the memory being started directly after generation of the evaluation order.

20. The method according to claim 18, further comprising the data base storing evaluation orders in a sequence and the control selecting one of the evaluation orders stored in the data base according to this sequence and depending upon the selected evaluation order starting the evaluation program stored in the memory with the evaluation program accessing original data stored in the data base depending upon the evaluation order.

21. The method according to claim 18, further comprising an evaluation apparatus forming a self-contained physical unit and comprising the memory and the control, the data base and the evaluation apparatus being connected to one another for the exchange of data.

22. The method according to claim 18, further comprising at least one evaluation order exchanging data from the system with another system.

* * * * *